United States Patent [19]
Srinivasan et al.

[11] Patent Number: 5,830,431
[45] Date of Patent: Nov. 3, 1998

[54] RADIOLABELED PEPTIDE COMPOSITIONS FOR SITE-SPECIFIC TARGETING

[75] Inventors: Ananthachari Srinivasan, St. Charles; Mary Marmion Dyszlewski, Maryland Heights; Joseph E. Bugaj; Jack L. Erion, both of St Charles, all of Mo.

[73] Assignee: Mallinckrodt Medical, Inc., St. Louis, Mo.

[21] Appl. No.: 480,373

[22] Filed: Jun. 7, 1995

[51] Int. Cl.$^6$ ............................ A61K 51/00; A61M 36/14
[52] U.S. Cl. ..................... 424/1.69; 424/1.65; 424/1.11; 530/300; 530/311; 530/317
[58] Field of Search .................................. 424/1.11, 1.53, 424/1.69, 9.1, 1.65; 530/300, 311, 324–330, 317; 534/10–16; 206/223, 569, 570

[56] References Cited

U.S. PATENT DOCUMENTS

| | | |
|---|---|---|
| 4,282,143 | 8/1981 | Sarantakis . |
| 4,395,403 | 7/1983 | Bauer et al. ......................... 424/177.1 |
| 4,440,904 | 4/1984 | Sarantakis . |
| 4,585,755 | 4/1986 | Morgan et al. ........................... 514/11 |
| 4,725,577 | 2/1988 | Schally et al. . |
| 5,225,180 | 7/1993 | Dean et al. . |
| 5,411,943 | 5/1995 | Bogden .................................. 530/327 |
| 5,650,134 | 7/1997 | Albert et al. ........................... 424/1.69 |

FOREIGN PATENT DOCUMENTS

| | | |
|---|---|---|
| 2225579 | 6/1990 | United Kingdom . |
| 9006949 | 6/1990 | WIPO . |

OTHER PUBLICATIONS

Patel (1990), The New England Journal of Medicine, vol. 323, No. 18, pp. 1274–1276, "Somatostatin–Receptor Imaging for the Detection of Tumors".

Kvols et al (1986), The New England Journal of Medicine, vol. 315, No. 11, pp. 663–666, "Treatment of the Malignant Carcinoid Syndrome".

Ellison et al (1986), The American Journal of Medicine, vol. 81, Suppl. 6B, pp. 56–63, "Characterization of the in Vivo and in Vitro Inhibition of Gastrin Secretion from Gastrinoma by a Somatostatin Analogue (SMS 201–995)".

Bauer et al (1982), Life Sciences, vol. 31, pp. 1133–1140, "SMS 201–995: A very Potent and Selective Octapeptide Analogue of Somatostatin With Prolonged Action".

de Jong et al (1992, thesis report), pp. 89–101, Radiopharmaceuticals for Scintigraphy of Somatostatin Receptor Positive Tumors, Chapter 7: Kinetic handling of $[^{125}I-Tyr^3]$–octreotide and $[^{111}In-DTPA-D-Phe^1]$–octreotide by the isolated perfused rat liver.

*Primary Examiner*—John Kight
*Assistant Examiner*—Dameron Jones
*Attorney, Agent, or Firm*—Jeffrey S. Boone; Thomas P. McBride

[57] ABSTRACT

This invention relates to radiolabeled peptide compositions for radiopharmaceutical use and, more specifically, to radiolabeled peptides for diagnostic or therapeutic use having an unmodified carboxy terminal amino acid. The radiopharmaceutical composition may be used for targeting a selected biological site. The radiolabeled peptide is characterized by having its carboxy terminal amino acid in its carboxylic acid form and the peptide is coupled to a diagnostic or therapeutic radionuclide by a chelating agent. The radiopharmaceutical composition preferably comprises a radiolabeled peptide selected from the group consisting of somatostatin, an analog of somatostatin, a derivative of somatostatin and peptides capable of binding to the somatostatin receptor, where the peptide is coupled to a diagnostic or therapeutic radionuclide by a chelating agent has its carboxy terminal amino acid in its carboxylic acid form.

19 Claims, No Drawings

# RADIOLABELED PEPTIDE COMPOSITIONS FOR SITE-SPECIFIC TARGETING

FIELD OF THE INVENTION

This invention relates in general to radiolabeled peptide compositions for radiopharmaceutical use and, more specifically, to a radiolabeled peptide for diagnostic or therapeutic use having an unmodified carboxy terminal amino acid.

BACKGROUND OF THE INVENTION

Various radiolabeled peptide compositions have been developed or are under development for site-specific targeting of a therapeutic or diagnostic radionuclide. The general principle involves attaching a selected radionuclide to a peptide having a high specificity for a particular organ or tissue so that the organ or tissue can be scintigraphically imaged for diagnostic purposes or treated by a therapeutic radioisotope. This field of research has shown particular applicability for tumor imaging and treatment. Particularly desirable biological sites include neuroendocrine tumors such as abdominal tumors, and small cell lung carcinomas, brain tumors, prostate tumors, breast tumors, colon tumors, and ovarian tumors.

Some of the known radiolabeled site-specific peptides include an In-111 labeled pentetreotide (Mallinckrodt Medical, Inc.) that targets neuroendocrine tumors, a technetium 99m labeled somatostatin or somatostatin analog (U.S. Pat. No. 5,225,180, International Publication No. 94/00489) for imaging tissues or organs presenting somatostatin receptors, an In-111 labeled somatostatin analog identified as RC-160 (W. A. P. Breeman, et al., European J. Nuc. Medicine, 21, 328 (1994)), and technetium 99m labeled cyclic peptides (International Publication No. 94/00489). Each of these peptides or peptide derivatives have been prepared for use as a radiopharmaceutical by modifying the carboxy terminal amino acid to either an alcohol or an amide. It was believed that this was necessary to prevent degradation by peptidases and to provide a longer residence time of the peptide in the blood.

SUMMARY OF THE INVENTION

The present invention is directed to a radiopharmaceutical composition for targeting a selected biological site. The composition comprises a radiolabeled peptide selected from the group consisting of somatostatin, vasointestinal peptide (VIP), pituitary adenylate cyclase activating polypeptide (PACAP), Substance P, enkephalins, neurokinins and analogs or derivatives of any of the above as well as peptides capable of binding to the corresponding receptor of any of the above peptides. The radiolabeled peptide is characterized by having its carboxy terminal amino. acid in its carboxylic acid form and the peptide is coupled to a diagnostic or therapeutic radionuclide by a chelating agent.

In one significant aspect of the invention, a radiopharmaceutical composition comprising a radiolabeled peptide selected from the group consisting of somatostatin, an analog of somatostatin, a derivative of somatostatin and peptides capable of binding to the somatostatin receptor, where the peptide is coupled to a diagnostic or therapeutic radionuclide by a chelating agent, is provided. The radiolabeled peptide is characterized by having its carboxy terminal amino acid in its carboxylic acid form. Preferably, the radiopharmaceutical is D-Phe-Cys-Phe-D-Trp-Lys-Thr-Cys-Thr-OH labeled with In-111 or Technetium 99m through a chelating agent.

In a further significant aspect of the invention, a method for targeting a radiolabeled peptide selected from the group consisting of somatostatin, an analog of somatostatin, a derivative of somatostatin and peptides capable of binding to the somatostatin receptor to a somatostatin receptor is provided wherein the radiolabeled peptide has its carboxy terminal amino acid in its carboxylic acid form and is coupled to a diagnostic or therapeutic radionuclide by a chelating agent and the radiolabel is detected at the selected biological site by scintigraphic means.

Among the many advantages found to be achieved by the present invention include the following: the provision of a radiopharmaceutical composition comprised of a radiolabeled peptide or analog or derivative thereof that retains its carboxy terminal amino acid in its carboxylic acid form; the provision of a radiopharmaceutical composition for diagnostic or therapeutic applications that provides enhanced blood and liver clearance when compared to similar compositions having a modified carboxy terminal ainio acid; the provision of a radiopharmaceutical composition that permits faster tumor visualization in diagnostic applications than similar compositions having a modified carboxy terminal amino acid; the provision of a radiopharmaceutical composition that exhibits increased tumor uptake and retention than similar compositions having a modified carboxy terminal amino acid; and the provision of a method for targeting a radiolabeled peptide of the present invention to a selected biological site or tissue for diagnostic or therapeutic applications.

DETAILED DESCRIPTION OF THE PREFERRED EMBODIMENTS

It has been discovered that the efficacy of a radiolabeled peptide for targeting a selected biological site for diagnostic or therapeutic applications is significantly improved by retaining the carboxy terminal amino acid of the peptide in its carboxylic acid form. Surprisingly, a radiolabeled peptide of the present invention having an unmodified carboxy terminal amino acid exhibits improved in vivo properties when compared to corresponding radiolabeled peptides that have been specifically modified to remove the carboxylic acid at the carboxy terminal amino acid. In particular, the radiolabeled peptides of this invention display improved blood and liver clearance as well as improved biological site uptake and retention time. Accordingly, the present invention provides a radiopharmaceutical composition for targeting a selected biological site comprising a radiolabeled peptide selected from the group consisting of somatostatin, vasointestinal peptide (VIP), pituitary adenylate cyclase activating polypeptide (PACAP), Substance P, enkephalins, neurokinins and analogs or derivatives of any of the above as well as peptides capable of binding to the corresponding receptor of any of the above peptides wherein the radiolabeled peptide has its carboxy terminal amino acid in its carboxylic acid form and the peptide is coupled to a diagnostic or therapeutic radionuclide by a chelating agent.

The peptides used in conjunction with the present invention can be obtained by known isolation and purification protocols from natural sources, can be synthesized by standard solid or solution phase peptide synthesis methods according to the known peptide sequence of the peptide, or can be obtained from commercially available preparations. Included herein are peptides that exhibit the biological binding properties of the native peptide and retain the specific binding characteristics of the native peptide. Derivatives and analogs of the peptide, as used herein, include modifications in the composition, identity and derivitization of the individual amino acids of the peptide provided that the peptide retains the specific binding properties of the native peptide. Examples of such modification would include, modification of any of the amino acids to include the D-stereoisomer, substitution in the aromatic side chain of an aromatic amino acid, derivitization of the amino or carboxyl groups in the sidechains of an amino acid containing such a group in a sidechain, substitutions in the amino or carboxy terminus of the peptide, linkage of the peptide to a second peptide or biologically active moiety, and cyclization of the peptide (G. Van Binst and D. Tourwe, Peptide Research, 5, 8 (1992)). In a preferred embodiment, the peptide used to prepare the radiopharmaceutical composition of the present invention is somatostatin, derivatives of somatostatin, analogs of somatostatin or peptides that bind to the somatostatin receptor wherein the carboxy terminal amino acid is in its carboxylic acid form. More preferably, the peptide is D-Phe-Cys-Phe-D-Trp-Lys-Thr-Cys-Thr-OH (peptide 1) or D-Phe-Cys-Tyr-D-Trp-Lys-Thr-Cys-Thr-OH (peptide 2).

The peptide selected for use in the radiopharmaceutical of the present invention is radiolabeled by coupling a chelating agent to the peptide. The chelating agent is capable of covalently binding a selected radionuclide thereto. The chelating agent and radionuclide are coupled to the peptide and chelating agent, respectively, in a manner that does not interfere or adversely affect the binding properties or specificity of the peptide. The use of various chelating agents for radiolabeling peptides is well known in the art. Suitable chelating agents generally include those which contain a tetradentate ligand with at least one sulfur group available for binding the metal radionuclide such as the known $N_3S$ and $N_2S_2$ ligands. More particularly, chelating groups that may be used in conjunction with the peptides of the present invention include 2,3-bis(mercaptoacetamido)propanoate (U.S. Pat. No. 4,444,690), S-benzoylmercaptoacetylglycylglycylglycine (U.S. Pat. No. 4,861,869), dicyclic dianhydrides such as DTPA and EDTA and derivatives thereof (U.S. Pat. No. 4,479,930), NS chelates containing amino groups to enhance chelation kinetics (U.S. Pat. No. 5,310,536), $N_2S_2$ chelates as described in U.S. Pat. No. 4,965,392, the $N_3S$ chelates as described in U.S. Pat. No. 5,120,526, and the $N_2S_2$ chelates containing cleavable linkers as described in U.S. Pat. No. 5,175,257. All of the patents referred to above and the teachings therein are hereby incorporated by reference hereto. The chelating agent is coupled to the peptide by standard methodology known in the field of the invention and may be added at any location on the peptide provided that the biological activity of the peptide is not adversely affected. Preferably, the chelating group is covalently coupled to the amino terminal amino acid of the peptide. The chelating group may advantageously be attached to the peptide during solid phase peptide synthesis or added by solution phase chemistry after the peptide has been obtained. Preferred chelating groups include DTPA, carboxymethyl DTPA, tetradentate ligands containing a combination of N and S donor atoms or N donor atoms.

Any radionuclide having diagnostic or therapeutic value can be used as the radiolabel for the peptides of this invention. In a preferred embodiment, the radionuclide is a γ-emitting or β-emitting radionuclide selected from the lanthanide or actinide series of the elements. Positron-enitting radionuclides, e.g. 68Ga, may also be used.

Suitable γ-emitting radionuclides include those which are useful in diagnostic imaging applications. The γ-emitting radionuclides preferably have a half-life of from 1 hour to 40 days, preferably from 12 hours to 3 days. Examples of suitable γ-emitting radionuclides include 67Ga, 111In, 99mTc, 169Yb and 186Re. Most preferably, the radionuclide is 99mTc.

Suitable β-emitting radionuclides include those which are useful in therapeutic applications. Examples include 90Y, 67Cu, 186Re, 188Re, 169Er, 121Sn, 127Te, 143Pr, 198Au, 109Pd, 165Dy, 32P, 142Pr, and 153Sm. The γ-emitting radionuclide preferably has a half-life of from 2 hours to two weeks, and more preferably from about 2 hours to 100 hours.

The peptide/chelate conjugates of the invention are labeled by reacting the conjugate with the selected radionuclide, e.g. a metal salt, preferably water soluble. The reaction is carried out by known methods in the art preferably using a reducing agent (e.g., stannous chloride) and a transfer agent (e.g., tartrate, gluconate, citrate or mannitol) as described in Examples 4 and 5 hereinbelow.

The radiolabeled peptide/chelate conjugates of the invention and their pharmaceutically acceptable salts are useful as a diagnostic imaging agent or in therapeutic applications. The radiolabeled peptide/chelate conjugate is prepared in a pharmaceutically acceptable carrier, e.g. saline or blood plasma, and is administered to an individual in a diagnostically or therapeutically effective amount as determined using standard methods known to those in the art. The carrier may also contain pharmaceutically acceptable adjunct materials such as salts, buffers, preservatives and the like. Preferably, the radiopharmaceutical composition of the present invention is provided in a kit whereby the radionuclide is provided in one vial and the peptide/chelating group conjugate is provided in a second vial and the contents mixed just prior to administration. The mixture may be heated if necessary to effect complete labelling. The provision of such radiolabeled complexes in kit form and the preparation of the final radiolabeled product are standard and routine in the field of nuclear medicine. The final radiopharmaceutical product should be of high radiochemical purity, preferably greater than 95%, and at least greater than 90%, as determined by standard protocols known in the art.

The radiolabeled complex is prepared to provide a radioactive dose of between about 0.05 mCi and about 40 mCi, preferably about 1 mCi to about 20 mCi, to the individual in accordance with standard radiopharmaceutical dosing determinations. As used herein, "a diagnostically effective amount" means an amount of the radiopharmaceutical sufficient to permit its detection by scintigraphic means and "a therapeutically effective amount" means an amount sufficient to effect a therapeutic treatment at the targeted biological site. The radiolabeled peptides may be administered intravenously in any conventional medium for intravenous injection. Imaging of the biological site may be effected within about 2–5 minutes post-injection, but may also take place several hours post-injection. Any conventional method of imaging for diagnostic purposes may be utilized.

The following examples describe preferred embodiments of the invention. Other embodiments within the scope of the claims herein will be apparent to one skilled in the art from consideration of the specification or practice of the invention as disclosed herein. It is intended that the specification, taken together with the examples, be considered exemplary only, with the scope and spirit of the invention being indicated by the claims.

EXAMPLE 1

This example describes the synthesis of a peptide/chelating group conjugate of the present invention wherein the carboxy terminal amino acid retains its carboxylic acid.

A peptide/chelating group conjugate comprised of D-Phe-Cys-Phe-D-Trp-Lys-Thr-Cys-Thr-OH as the peptide (peptide 1) and DTPA as the chelating group bound at the amino terminus of the peptide 1 sequence was synthesized on a 0.2–0.3 mmole scale using an Applied Biosystems Model 431A Peptide synthesizer. Fmoc-O-t-butyl threonine loaded-SASRIN resin (0.3–0.4 mmol/g of the resin) (Bachem Biosciences) was used. After successive condensation with the amino acids, the N-terminal Fmoc protecting group was removed according to the general protocols in the synthesizer. The solid phase synthesis was continued with 1,1,4-Tris(t-butyloxycarbonylnethyl)-7,7-bis(carboxymethyl)-1,4,7-triazaheptane. After the synthesis was completed, the product, the mono addition product DTPA-peptide, was cleaved using a solution of trifluoroacetic acid:water:anisole:triisopropylsilane for 1–6 hours at room temperature. The product was precipitated by ether and purified by C-18 reverse phase chromatography. Cleavage, deprotection and LC purification yielded mono-DTPA-peptide 1 in high purity, m/e 1409 (M+1).

EXAMPLE 2

This example illustrates the synthesis of a peptide/chelating group conjugate having its carboxy terminal amino acid in its carboxylic acid form which is useful in connection with the present invention.

DTPA-peptide 2 was synthesized according to the procedure set forth in Example 1 except that the peptide synthesized was peptide 2. Cleavage, deprotection and LC purification yielded mono-DTPA-peptide 2 in high purity, m/e 1425 (M+1).

EXAMPLE 3

This example illustrates the synthesis of a peptide/chelating group conjugate having its carboxy terminal amino acid in its carboxylic acid form which is useful in connection with the present invention.

A peptide/chelating group conjugate comprised of peptide 1 as the peptide and an $N_3S$ ligand (as shown below) as the chelating group bound at the amino terminus of peptide 1 was synthesized by a combination solid-solution phase method. H-Lys(ε-Troc)-Glu-Aha-D-Phe-Cys-Phe-D-Trp-Lys(ε-Troc)-Thr-Cys-Thr-OH (peptide 3) was synthesized from Fmoc-O-t-butyl threonine loaded-SASRIN resin (0.3–0.4 mmol/g of the resin) (Bachem Biosciences) according to the general procedure described in Example 1 above. The compound was characterized by mass spectra, m/e 1752 (M+1). To a solution of the above peptide 3 in dimethylformamide containing triethyl amine (10 mL of DMF/mmole of the peptide and 1 mL of triethylamine/mmol of the peptide), S-tetrahydropyranyl-mercaptoacetic acid succinimidate ester was added and the solution was stirred at room temperature. The solvent was removed and the product isolated by C-18 flash chromatography. Product from this step (THP-S-MA-Lys(ε-Troc)-Glu-Aha-D-Phe-Cys-Phe-D-Trp-Lys(ε-Troc)-Thr-Cys-Thr-OH) was stirred with Zn powder/THF/water to remove the Troc protecting groups to give the final product:

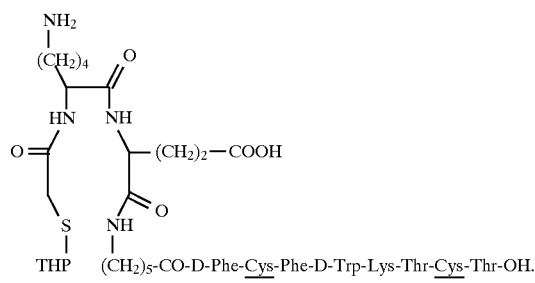

EXAMPLE 4

This example illustrates the synthesis of a peptide/chelating group conjugate having its carboxy terminal amino acid in its carboxylic acid form which is useful in connection with the present invention.

A peptide/chelating group conjugate comprised of peptide 2 as the peptide and an $N_3S$ ligand (as shown below) as the chelating group bound at the amino terminus of peptide 2 was synthesized by a combination solid-solution phase method. H-Lys(ε-Troc)-Glu-Aha-D-Phe-Cys-Tyr-D-Trp-Lys(ε-Troc)-Thr-Cys-Thr-OH (peptide 4) was synthesized from Fmoc-O-t-butyl threonine loaded-SASRIN resin (0.3–0.4 mmol/g of the resin) (Bachem Biosciences) according to the general procedure described in Example 1 above. The compound was characterized by mass spectra, m/e 1752 (M+1). To a solution of the above peptide 4 in dimethylformamide containing triethyl amine (10 mL of DMF/mmole of the peptide and 1 mL of triethylamine/mmol of the peptide), S-tetrahydropyranyl-mercaptoacetic acid succinimidate ester was added and the solution was stirred at room temperature. The solvent was removed and the product isolated by C-18 flash chromatography. Product from this step (THP-S-MA-Lys(ε-Troc)-Glu-Aha-D-Phe-Cys-Tyr-D-Trp-Lys(ε-Troc)-Thr-Cys-Thr-OH) was stirred with Zn powder/THF/water to remove the Troc protecting groups to give the final product:

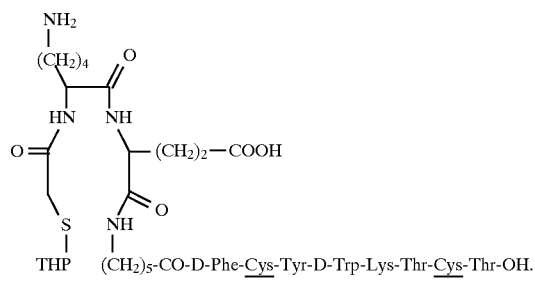

EXAMPLE 5

This example describes the radiolabelling of the DTPA-peptide 1 and DTPA-peptide 2 peptide/chelating group conjugates produced in Examples 1 and 2 above, respectively.

Five micrograms of either DTPA-peptide 1 or DTPA-peptide 2 was dissolved in water containing 0.05N HCl containing 0.624 mg sodium acetate and 0.440 mg ascorbic acid. Three mCi of In-111, as Indium chloride, was added. Labeling was effected at room temperature and was complete within 15 minutes. The final reaction volume was 200 μl and the pH was 4. The yield of the radiolabeled peptide 1 or 2 was >98% and the purity was also >98%.

EXAMPLE 6

This example describes the Tc-99m-labeling of the $N_3S$-peptide 1 peptide/chelating group conjugate described in Example 3.

Tc-99m labeling was performed using commercially available Merck-Frosst kit. The kit components were dissolved in 1 mL of water. In a separate vial containing 1 mL of pertechnetate, 30 mCi, from a commercially available generator, 100 μL of the solution from Merck-Frosst kit was added and the solution allowed to stand for 15 minutes. To this solution, 100 μg of the $N_3S$-peptide 1 product was added and the solution heated at 100° C. for 15–20 minutes. The solution was ready for administration after filtration through a sterile filter.

EXAMPLE 7

This example illustrates the improved properties of a radiolabeled peptide of the present invention that retains its C-terminal amino acid carboxylic acid as compared to a commercially available In-111 labeled pentatreotide neuroendocrine tumor imaging agent offered by Mallinckrodt Medical, Inc. under the trademark Octreoscan®.

Male Lewis rats ware implanted with CA20948 tumor material in the left flank area approximately 14–18 days prior to the injection of the radiolabeled compound(s) to establish a viable tumor mass that was expressing somatostatin receptors. On the day of the study the rats (n=3/group) receive an intravenous dose of the In-111 complex(s), the specific activity of the preparation was about 2800 Ci/mmol., and the animals were sacrificed at 1, 4 and 24 hours post injection. The following organs/tissues were removed and quantitated for uptake of the radio-tracer: blood, liver, spleen, heart, muscle, kidneys, small intestine, stomach, thyroid, bone (femur), adrenals, pancreas and tumor. At 24 hours, the feces and urine were also collected and counted to determine the routes of excretion and overall clearance patterns of the complex(s). Additionally, two rats were injected for metabolism studies to evaluate the in vivo stability of the complex, and two other rats were injected for visualization of the animals by gamma scintigraphy. The tissues were assayed for % injected dose (% ID) and % ID/gram of tissue to determine the overall biodistribution of the complex(s). From these values, ratios of target:non-target tissue values were assessed, which were calculated to determine the efficacy of the test composition relative to controls. The results are shown in Table 1 below.

TABLE 1

| Organ | $^{111}$In-DTPA-peptide 1 | $^{111}$n-DTPA-peptide 2 | Octreoscan ® |
|---|---|---|---|
| Time: 1 hr | | | |
| Blood | 0.115 (±0.004) | 0.062 (±0.002) | 0.154 (±0.004) |
| Liver | 0.187 (±0.011) | 0.042 (±0.002) | 0.12 (±0.019) |
| Kidney | 2.747 (±0.219) | 2.366 (±0.175) | 2.15 (±0.303) |
| Tumor | 2.004 (±0.121) | 2.689 (±0.1) | 0.57 (±0.10) |
| Pancreas | 2.788 (±0.156) | 6.776 (±0.6) | 0.57 (±0.106) |
| TU/BL. | 17 | 43 | 6 |
| Time: 4 hr | | | |
| Blood | 0.023 (±0.004) | 0.010 (±0.002) | 0.035 (±0.001) |
| Liver | 0.139 (±0.011) | 0.028 (±0.002) | 0.09 (±0.008) |
| Kidney | 3.664 (±0.219) | 2.275 (±0.101) | 2.06 (±0.011) |
| Tumor | 1.744 (±0.121) | 2.271 (±0.5) | 0.76 (±0.03) |
| Pancreas | 2.312 (±0.156) | 5.755 (±0.6) | 0.79 (±0.02) |
| TU/BL. | 76 | 227 | 59 |
| Time: 24 hr | | | |
| Blood | 0.009 (±0.004) | 0.008 (±0.002) | 0.004 (±0.001) |
| Liver | 0.107 (±0.011) | 0.021 (±0.002) | 0.029 (±0.008) |
| Kidney | 2.384 (±0.059) | 2.371 (±0.201) | 1.75 (±0.011) |
| Tumor | 1.074 (±0.058) | 1.492 (±0.5) | 0.33 (±0.03) |
| Pancreas | 1.312 (±0.081) | 2.659 (±0.6) | 0.43 (±0.02) |
| TU/BL. | 119 | 187 | 59 |

*the numbers in parentheses = standard deviations

These results illustrate the increased tumor uptake and retention time of a radiolabeled peptide having its carboxy terminal amino acid in its carboxylic acid form as compared to a commercially available radiolabeled peptide specific for the same tumor receptor as well as indicating faster clearance from the blood. Regarding the metabolism studies, the urine samples were analyzed by reverse phase HPLC and the results showed that the complexes were excreted without any significant decomposition.

What is claimed is:

1. A radiopharmaceutical composition for targeting a selected biological site, the composition comprising:
   a radiolabeled peptide selected from the group consisting of somatostatin, derivatives of somatostatin, analogs of somatostatin or peptides that bind to the somatostatin receptor, wherein the radiolabeled peptide has its carboxy terminal amino acid in its carboxylic acid form and the peptide is coupled to a diagnostic or therapeutic radionuclide by a chelating agent.

2. The composition of claim 1 wherein the peptide is D-Phe-Cys-Phe-D-Trp-Lys-Thr-Cys-Thr-OH.

3. The composition of claim 1 wherein the peptide is D-Phe-Cys-Tyr-D-Trp-Lys-Thr-Cys-Thr-OH.

4. The composition of claim 1 wherein the diagnostic radionuclide is Indium-111 or Technetium 99m.

5. The composition of claim 1 wherein the therapeutic radionuclide is selected from the group consisting of 90Y, 67Cu, 186Re, 188Re, 169Er, 121Sn, 127Te, 143Pr, 198Au, 109Pd, 165Dy, 32P, 142Pr, and 153Sm.

6. The composition of claim 1 wherein the chelating agent is a tetradentate ligand with at least one sulfur group available for binding the radionuclide.

7. The composition of claim 1 wherein the chelating agent is DTPA.

8. A method for targeting a radiopharmaceutical composition to a selected biological site presenting somatostatin receptors, the method comprising:
   administering a diagnostic amount of a radiolabeled peptide selected from the group consisting of somatostatin, derivatives of somatostatin, analogs of somatostatin or peptides that bind to the somatostatin receptor, wherein the radiolabeled peptide has its carboxy terminal amino acid in its carboxylic acid form and the peptide is coupled to a diagnostic radionuclide by a chelating agent; and
   detecting the radiolabel at the selected biological site.

9. The method of claim 8 wherein the peptide is D-Phe-Cys-Phe-D-Trp-Lys-Thr-Cys-Thr-OH.

10. The method of claim 8 wherein the peptide is D-Phe-Cys-Tyr-D-Trp-Lys-Thr-Cys-Thr-OH.

11. The method of claim 8 wherein the diagnostic radionuclide is Indium-111 or Technetium 99m.

12. The method of claim 8 wherein the chelating agent is a tetradentate ligand with at least one sulfur group available for binding the radionuclide.

13. The method of claim 8 wherein the chelating agent is DTPA.

14. A method for targeting a radiopharmaceutical composition to a selected biological site presenting somatostatin receptors, the method comprising:

administering a therapeutic amount of a radiolabeled peptide selected from the group consisting of somatostatin, derivatives of somatostatin, analogs of somatostatin or peptides that bind to the somatostatin receptor, wherein the radiolabeled peptide has its carboxy terminal amino acid in its carboxylic acid form and the peptide is coupled to a therapeutic radionuclide by a chelating agent.

15. The method of claim 14 wherein the peptide is D-Phe-Cys-Phe-D-Trp-Lys-Thr-Cys-Thr-OH.

16. The method of claim 14 wherein the peptide is D-Phe-Cys-Tyr-D-Trp-Lys-Thr-Cys-Thr-OH.

17. The method of claim 14 wherein the therapeutic radionuclide is selected from the group consisting of 90Y, 67Cu, 186Re, 188Re, 169Er, 121Sn, 127Te, 143Pr, 198Au, 109Pd, 165Dy, 32P, 142Pr, and 153Sm.

18. The method of claim 14 wherein the chelating agent is a tetradentate ligand with at least one sulfur group available for binding the radionuclide.

19. The method of claim 14 wherein the chelating agent is DTPA.

* * * * *